United States Patent [19]

Bryan

[11] Patent Number: 5,054,919

[45] Date of Patent: Oct. 8, 1991

[54] SEAL FOR HIGH PRESSURE AND SMALL VOLUME SAMPLE CELLS

[75] Inventor: Raymond G. Bryan, Reno, Nev.

[73] Assignee: Linear Instruments Corporation, Reno, Nev.

[21] Appl. No.: 307,766

[22] Filed: Feb. 7, 1989

[51] Int. Cl.[5] .............................................. G01N 1/10
[52] U.S. Cl. .................................... 356/246; 356/410
[58] Field of Search ................................ 356/246, 410

[56] References Cited

U.S. PATENT DOCUMENTS 3,597,096 8/1971 Burkhard ........................... 356/246
4,192,614 3/1980 deMey, II et al. .
4,588,893 5/1986 Vidrine et al. ................... 356/246 X
4,747,687 5/1988 Hoppe et al. .

Primary Examiner—Davis L. Willis
Assistant Examiner—Matthew W. Koren
Attorney, Agent, or Firm—Lyon & Lyon

[57] ABSTRACT

There is disclosed herein a cell assembly for a spectrophotometric analysis or detection of a substance within a small sample volume. The assembly includes a cell body with a small sample bore, along with windows engaging said body to allow radiation to pass through the sample bore and the windows. A sealing arrangement is provided for each window via a sealing washer which is loaded by two means. An inner portion of the sealing washer engages the window and is loaded by a first spring loaded assembly, such as a Belleville washer and plunger. An outer portion of the sealing washer is separately loaded by a ring pressed against the cell body.

12 Claims, 2 Drawing Sheets

SEAL FOR HIGH PRESSURE AND SMALL VOLUME SAMPLE CELLS

FIELD OF THE INVENTION

The present invention relates to the field of spectrophotometry, and more particularly to an improved sample cell assembly.

BACKGROUND OF THE INVENTION

Various forms of spectrophotometers and sample cells therefor are well-known. In these devices, radiation from a radiation source passes through a sample cell to a photodetector which measures the amount of radiation passed through the sample in the cell, and the output of the detector system is a measure of absorbance of a particular wavelength of radiation. The quantitative presence of certain materials in the sample fluid can be identified by particular wavelengths characteristically absorbed by such materials.

One area in which spectrophotometers and their detectors are particularly important is the field of chromatography, in which components of a sample are separated in a chromatographic column and radiation absorbance of the separated components is measured by the detector.

As background, chromatography is a method of separating a mixture of substances (the sample) by passing the mixture over or through a second substance or mixture of substances with which the components of the sample will have different molecular interactions. In liquid chromatography (LC), the sample is introduced into a flowing carrier, called the mobile phase, which takes the sample through the separating substance, called the stationary phase. Depending on the interaction between the sample and the stationary phase in the presence of the mobile phase, different components of the sample will take various lengths of time to flow through the stationary phase, thus being separated into distinct segments of the exiting flow. A detector is placed to monitor some particular characteristic of the mobile phase as it exits from the stationary phase. Based on the time taken to exit (time of elution) from the stationary phase, the presence of the monitored characteristic substances can be identified or qualitative analysis performed. By integrating an adjusted intensity of the output of the detector as a function of time over the presence of an existing component, the amount of the substance can be a determined or a quantitative analysis performed. Additionally, when the presence of a desired substance is detected, the flow can be diverted to a separate collection vessel for the duration of that component's segment. The liquid chromagraphic technique is widely used in a variety of applications, such as in industrial fields—pharmaceutical, polymers, explosives, dyes, vitamins; clinical fields—drug screens, protein analysis, toxicology, pollution; research—proteins, genetics, drugs, polymers, and so on.

The basic components of a liquid chromatographic system are mobile phase delivery, sample introduction, stationary phase column, detector, and data acquisition devices. Detection techniques include absorbance, refractive index, conductivity, pH, fluorescence, and so on. Absorbance detection is a highly sensitive wavelength selectable technique that can be used to detect almost any substances.

Turning particularly to absorbance detectors, different types of detectors can be fitted with a sample cell through which the mobile phase exiting the stationary phase flows for detection. Light at the selected wavelength passes through this flow from the source to a collection point, with some light being absorbed along the way. Sample cells differ in their contact materials, volume of fluid in the light path, and length of the light path through the fluid depending on the type of chromatography, sample components, mobile phase, sensitivity, and application.

Linear Instruments Corporation of Reno, Nev., for example, manufactures several models of absorbance detectors ranging from simple fixed wavelength units to microprocessor-controlled variable/multiple wavelength units. A variety of sample cells are available from this company and are interchangeable on any of the detectors ranging in size from 0.025 mm capillaries to 10 liter per minute preparative scale cells.

In the sample cells used in such devices, radiation transparent optical windows allow radiation from the source to pass through the cell to the detector. In a common spectrophotometric detector construction, radiation passes through an entrance window, through the cell through the enclosed sample volume and through an exit window to the detector. Typically, flat windows or plano convex lenses are used. U.S. Pat. No. 4,192,614 shows a detector assembly with flat windows at the entrance and exit openings in the cell. A lens can focus the radiation in a pattern which converges in the cell. Another form of cell construction is illustrated in U.S. Pat. No. 4,747,687.

Of the various components in a liquid chromatographic system, the detector is considered the most technologically limiting factor in expanding the use of LC. Although recent advances in LC detectors have greatly facilitated the growth of the LC technique, each advance seems to be met by new demands on this expanding analytical and separation method. For example, in preparative scale high performance liquid chromatography (HPLC), sample cells are required to accommodate greater flow rates and volumes than conventional HPLC cells can handle, while applications in microbore HPLC cause the cells to handle much lower rates and volumes. Column technology and its applications dictate the requirements for the LC detector.

A need has existed for a cell suitable for use in supercritical fluid chromatography (SFC). This technique is used to perform liquid chromatographic analysis on difficult to dissolve, large molecular chains. The mobile phase is at a temperature and pressure above its supercritical point, with typical examples being supercritical carbon dioxide and supercritical ammonia—substances that aggressively attack most material. Sample volumes for this type of analysis are small. To provide good sensitivity and chromatographic performance in this application, a cell compatible with 0.125 mm ID flow paths, 0.250 microliter volume, and 2 mm pathlength has been considered for use capable of repeated cycling from standard atmospheric conditions to 150 degrees Celsius and over 400 atmospheres pressure (about 6,000 psi). A cell to meet these requirements of internal size, temperature, and pressure, and to contain and withstand the deleterious effects of the supercritical fluid, must include an appropriate optical path and have an external geometry compatible with host products. Prior to the present invention, no cells have been capable of successfully and repeatedly operating with supercritical fluids on this scale.

It is common to have a cell for containing a specified sample volume of a substance, moving or stationary, into, out of, or through which suitable electromagnetic radiation is transmitted for the purpose of spectrophotometric analysis or detection of the substance within the sample volume. The present invention relates to a technique for sealing into place on the cell body one or more windows transparent to the radiation between the sample volume and the exterior of the cell to facilitate this analysis or detection. According to a specific exemplary embodiment according to the present invention, a seal washer compatible with conditions and substances existing within the sample volume is placed across the interface of the cell body and window and applies a load sufficient to make a pressure-tight fit at the contact area of the seal washer to window and seal washer to cell body.

For certain types of spectrophotometric analysis or detection, it is desirable for the sample volume to be small. Additionally, it may be desirable for the sample volume to be at high pressure or high temperature, or a combination of pressure and temperature, and for the pressure and temperature to be cycled repeatedly between standard atmospheric conditions and elevated values. Substances within the sample volume that are fluids at elevated pressure may be non-fluids at standard temperature and pressure, or may be supercritical fluids at an elevated temperature and pressure. The typical fluid used in analyses of this type is supercritical carbon dioxide.

For an analysis where a small volume of supercritical fluid is to be used, in addition to the requirements of size, temperature, pressure, and geometry on its configuration, the vessel must withstand the deleterious effects of the supercritical fluid as noted earlier and any other substances contained within the fluid. Previous cells have been unable to successfully and repeatedly operate with supercritical fluids employing other window sealing approaches.

SUMMARY OF THE INVENTION

According to the concepts of the present invention, a sample volume and radiation path is provided within a cell body and enclosed with one or more windows transparent to the radiation, and is made of materials impervious to the substance within the sample volume similar to prior cell designs. The concepts of the present invention provide the means to successfully operate in the supercritical fluid environment by sealing across the cell body and window interface on the far side from the sample volume with a seal washer of soft metal material able to withstand the temperature and pressure, and either impervious to the fluid or coated with a material impervious to the fluid. The seal washer further is loaded against the window and body by elements capable of independently making a pressure-tight fit at both the contact areas of the seal washer to window and seal washer to cell body.

Thus, appropriate seals are provided by applying two forces to different parts of a sealing member (seal washer) to thereby seal the sealing member with a cell body and the window therefor.

Locating the seal on the far side from the fluid causes an increase in fluid pressure to increase the load applied to thereby enhance the pressure tightness. Selection of the appropriate seal materials and loads applied, with no internal fluid pressure, insures no leakage after repeated pressurization cycles.

Further according to the concepts and exemplary embodiment of the present invention, the use of two individual loading elements allows both sealing surfaces to function independently and to insure that sufficient loads at each are always present for all internal fluid pressures, dimensional accumulations, and surface characteristics. Because the seal washer and associated loading elements are located away from the sample volume and radiation path, the sizes of these items are not interrelated or limited by the small sample volume and, thus, small sample volumes can be achieved.

An exemplary embodiment of the present cell is designed to operate with supercritical fluids and elevated temperatures and pressures in an absorbance monitor. Additionally, operation is possible with all less demanding applications of the same analysis technique on a volume of fluid. An exemplary cell is in the Linear Instruments 200 Series detectors and is identified as the 9550-0150 High Pressure Microbore cell. The cell has a volume of 0.250 microliters, a pathlength along the axis of radiation transmission of 2 mm, can withstand pressures in excess of 6,000 psi, temperatures in excess of 150 degrees Centigrade, and is intended for radiation with wavelengths between 190 and 800 nanometers.

The concepts of the present invention, thus may be described as a seal across the innerface of a cell window and cell body wherein the seal is loaded with two independent forces acting at each respective interface. A first loading element provides the first independent force to cause the sealing means to seal with the window, and the second force may be provided by a second independent loading element which causes the sealing means to seal with the cell body. The sealing means preferably can be formed of metallic sealing material.

Accordingly, a principal object of the invention is to provide an improved seal across the interface of a cell window and cell body.

Another object of the present invention to provide an improved cell for spectrophotometers and the like.

Another object of this invention is to provide a sample cell assembly having a small internal volume and capable of withstanding the effects of supercritical fluids.

These and other objects, features, and advantages of the present invention will become better understood through a consideration of the following description taken in conjunction with the drawings.

BRIEF DESCRIPTION OF DRAWINGS

FIG. 3 is a cross-sectional view of a high-pressure sealing ring thereof; and

FIG. 4 is a cross-sectional view of a seal washer thereof.

DETAILED DESCRIPTION OF PREFERRED EMBODIMENT

Figure 1:
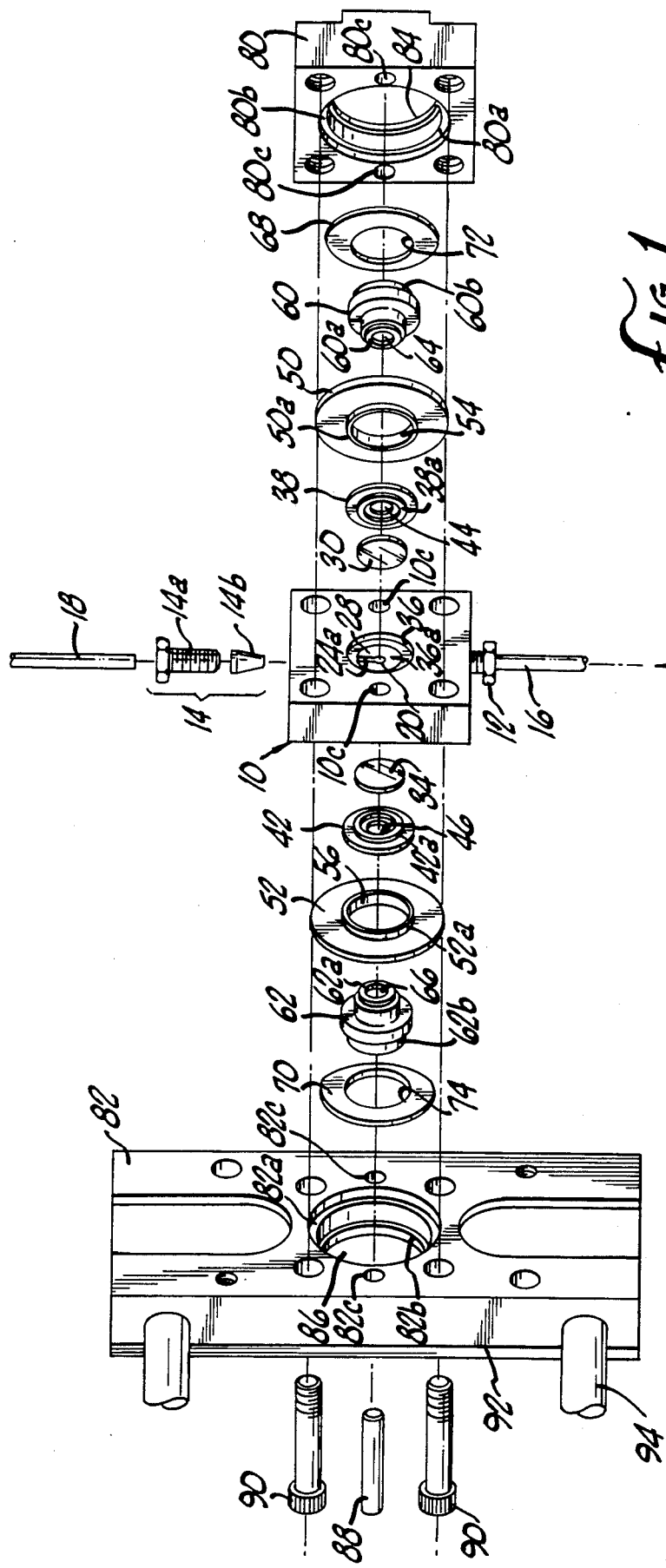
FIG. 1 is an exploded view of the sample cell assembly according to the present invention.

Turning now to the drawings and first to FIG. 1, an exemplary embodiment of a high pressure microbore assembly is illustrated, comprising a cell body 10 having suitable fittings 12 and 14 for respective inlet and outlet tubes 16 and 18. An exemplary fitting 14 comprises a fitting nut 14a and a ferule 14b. The cell body includes a sample bore 20 (note also FIG. 2) which forms the volume and pathlength for the sample fluid being analyzed, as well as suitable passageways 22a–22b and 24a–24b communicating with the passageway for providing fluid flow between the tubes 16 and 18. The cell body 10 is preferably machined from stainless steel to have the configuration shown in FIGS. 1 and 2. It will be seen from FIG. 2 that a passageway 16a in the inlet tube 16 communicates with the fluid flow inlet passageways 22a–b to the sample bore 20, and from the sample bore 20 through the passageways 24a–b to passageway 18a of the outlet tube 18.

Figure 2:
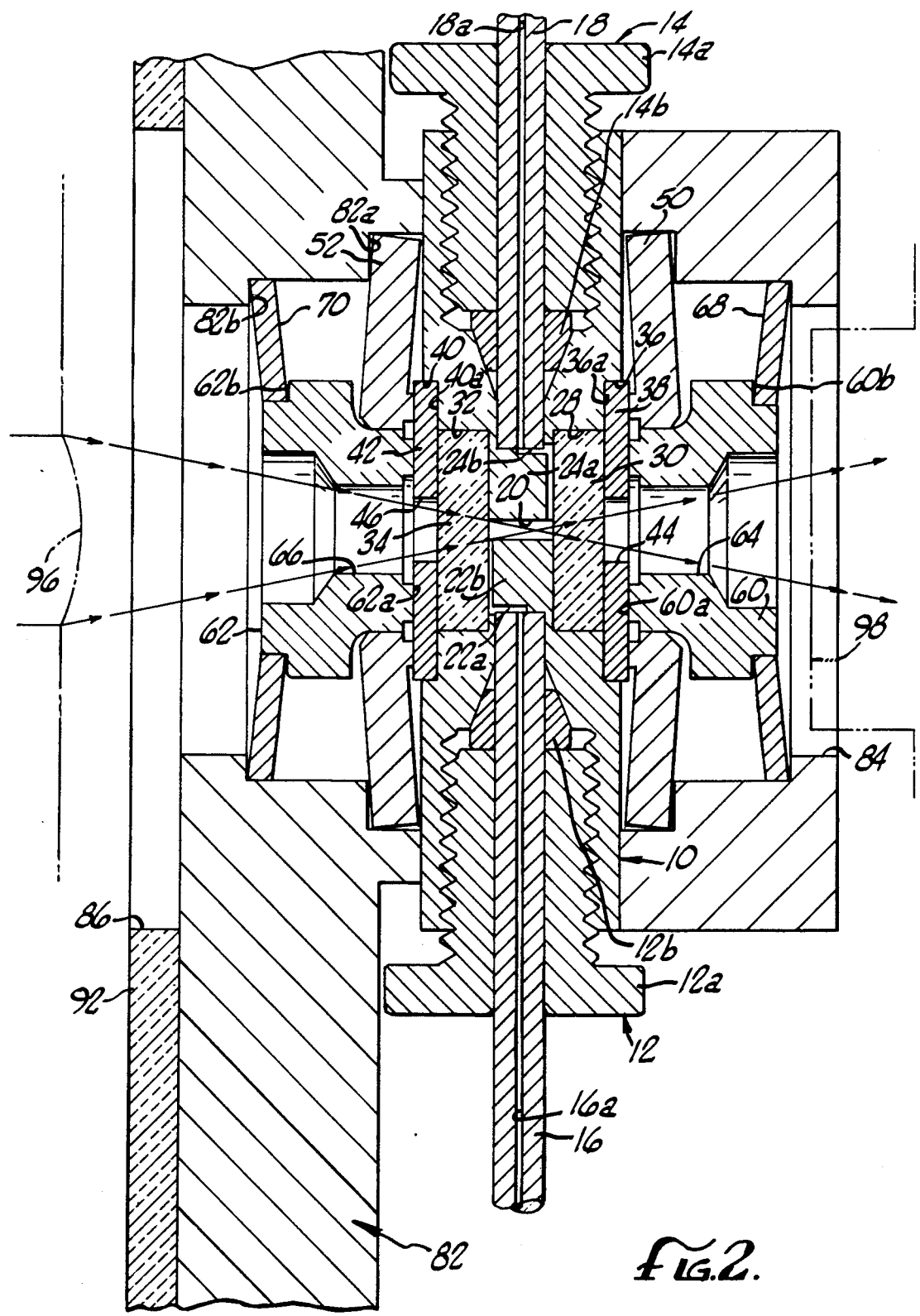
FIG. 2 is a detailed cross-sectional view thereof.

As will appear subsequently, the cell body 10 is essentially symmetrical. The cell body 10 further includes a bore or circular receptacle 28 for receiving a window 30 as seen in FIG. 2. A like receptacle 32 is provided in the left side of the sample cell body 10 for receiving a second window 34. These windows preferably are formed from uv grade sapphire with zero degree crystal orientation, and with a flatness of one to two fringes and parallel to 0.0002". A typical diameter range is 0.2470–0.2475" and a thickness of 0.064".

These windows enclose the sample volume of the bore 20 and passageways 22b and 24a, while allowing the transmission of radiation through the enclosed fluid.

Further bores or receptacles 36 and 40 are provided in the right and left sides, respectively, of the body 10 for receiving first seal washers 38 and 42. These first seal washers 38 and 42 are further shown in cross-section detail in FIG. 4, and each is formed of soft copper which has been gold-plated. Each of these seals includes a respective aperture 44, 46 for transmission of the radiation. Each of these seals 38 and 40 spans the interface between the respective windows 30, 34 and the right and left faces 36a and 40a of the cell body 10. These seals 38 and 42 comprise high-pressure sealing washers and each includes a circular projection 38a, 42a as seen in FIGS. 1 and 4 (not shown in FIG. 2).

These seals 38 and 42 are made of soft materials, such as copper, to be able to make a seal and withstand the fluid pressure, and each is plated, such as with gold, with a material resistant to the fluid to be contained within the sample cell. The selection of a soft material is necessary so a seal can be made at reasonable seating stresses, but the material cannot be a conventional elastomeric sealing material because the material would tend to creep and extrude at the pressures involved and most would dissolve in the supercritical fluids.

The next components are rings 50 and 52, which act as stiff spring washers to apply a known load sufficient to insure a pressure-tight fit between the seals 38, 42 and the cell body 10. These rings include flanges 54 and 56, and include circular projections 50a and 52a which bear against the outer faces of respective seals 38 and 42.

Plungers 60 and 62 are next provided, each with apertures 64, 66 for the transmission of radiation, and each with circular ridges 60a and 62a which bear against the outer faces of the respective seals 38 and 42. Each of the plungers 60, 62 includes an outer shoulder 60b and 62b. Respective Belleville washers 68 and 70 are provided and these bear against the respective shoulders 60b and 62b of the plungers 60 and 62. These washers likewise have openings 72 and 74 for mating with the shoulders 60b and 62b of the plungers.

A cap 80 is provided at the right side of the assembly and a holder 82 is provided at the left side of the assembly. Each has an appropriate configuration for bearing against the Belleville washers 68, 72 and the rings 50 and 52 for causing the windows 30, 34 to be appropriately sealed and held against the cell body 10. In this regard, the cap 80 has a first outer shoulder 80a for engaging the outer edge of the ring 50, and includes an inner shoulder 80b for engaging the outer edge of the Belleville washer 68, all as shown in detail in the cross-sectional view of FIG. 2. The cap 80 includes a suitable opening 84 for the transmission of radiation.

In a similar manner, the holder 82 includes an outer shoulder 82a which bears against the outer edge of the left-hand ring and includes an inner shoulder 82b which bears against the outer edge of the Belleville washer 70. The holder 82 also includes an aperture 86 for the transmission of radiation. The components are suitably aligned by dowel pins 88 which extend through aligned apertures 82c in the holder 82, 10c in the body 10 and 80c in the cap 80. Similarly, bolts 90 extend through apertures in the holder 82 and the cell body 10 and are threaded into internally threaded apertures in the cap 80 to secure the entire assembly together. The holder 82 is the means by which the overall assembly is secured to the instrument, and the holder may have a back cover 92 of insulating material, such as polycarbonate, and may include Tygon tubing 94 through which fluid of a suitable temperature may flow to enable the holder 82 to function as a heat exchange block.

The cap 80 and holder 82 transfer a given deflection to the Belleville washers 68 and 70 resulting in a load sufficient to make a pressure-tight fit between the seal washer 38 and window 30, and the washer 42 and the window 34 with and on both sides of the cell body 10. The cap 80 and holder 82 apply the required deflection to the Belleville washer 68 and the ring 50, and to the Belleville washer 70 and the ring 52.

Dashed lines 96 in FIG. 2 represent a lens for appropriately focusing the radiation into the assembly and through the sample bore 20 to a suitable detector assembly indicated by dashed lines 98 to the right in FIG. 2.

The following provides examples of components of the cell assembly of an exemplary embodiment. The body 10 may be machined from 316 stainless steel flat stock, and the cap 80 and holder 82 machined from 7075-T6 aluminum flat stock. As noted earlier, the windows 30 and 34 are formed from sapphire. The sealing washers 38 and 42 are formed from gold plated soft copper. For example, each may be 24-ounce, 0.032 thick UNS-C11000 soft copper ASTM-B-152, and with a heavy gold plating of 100 microns thick minimum, 23 carat 99.997 pure minimum. A typical thickness of the sealing washers 38 and 42 is 0.032", with the projection or rim adding an additional 0.0019", and a diameter of 0.375". The rings 50 and 52 may be formed from 0.750" diameter 17-4 PH stainless steel round stock, and suitably hardened. A typical thickness is 0.06", with the rim 52A being an additional 0.006". The plungers 60 and 62 may be formed from 0.375 diameter, 303 stainless steel stock. The Belleville washers 68 and 70 may have an outside diameter of approximately 0.625", 0.047" thick and be formed of stainless steel type 302 and with a typical uncompressed height of 0.059.".

From the foregoing, it will be apparent that a seal is provided by washers 38 and 42 on each window across the cell body to window interface on the far side from the sample volume; that is, a seal is formed between (i) the window 30 and the washer 38 and (ii) the shoulder 36a and washer 38 on the right side, and between (i) the window 34 and washer 42 and (ii) the shoulder 40a and washer 42 on the left side, as seen in FIGS. 1 and 2. The washers 38 and 42 are formed of soft copper, as noted earlier, so as to withstand the high internal pressures but to keep the required sealing stresses low, especially in contact with sapphire windows. These washers 38 and 42 are gold plated to provide an inert surface in contact with the fluid while not altering the sealing characteristics. The washers 38 and 42 are loaded against (a) the windows 30 and 34 and (b) the shoulders 36a and 40a of the body 10 by elements capable of independently making a pressures tight fit at both the contact area of the washer to window and the washer to cell body.

The use of two individual loading elements, namely (i) the rings 50 and 52 and (ii) the Belleville washers 68 and 70 with plungers 60 and 62 allow both sealing surfaces (washer to window and washer to cell body) to function independently and to insure that sufficient loads at each surface are always present for all internal fluid pressures, dimensional accumulations, and surface characteristics. Because the seals and associated loading elements are located away from the sample volume and light path, the size of the items involved is not tied to the small size of the sample volume (20) and, thus, suitable seals and loading elements can be provided while small sample volumes are maintained.

Thus, it can be seen that, for the right-hand side of the assembly, the cap 80 loads against (a) the ring 50 and (b) the Belleville washer 68. The ring 50, in turn, applies a load against the outer periphery of the washer 38 to insure the washer to cell body seal at shoulder 36a; whereas, the Belleville washer 68, via the plunger 60, loads the inner section of the washer 38 against the window 30 to insure the washer to window seal. The same sealing arrangement occurs on the left-hand side of the assembly as loaded by the holder 82 instead of the cap 80. Simply stated, one loading element (the ring 50 or 52) loads and seal the washer 38 or 42 against the shoulder 36a or 40a of the cell body 10 to insure the washer to cell body seal, and another element (the Belleville washer 68 or 70 through the respective plunger 60 or 62) insures the seal between the washer 38 or 42 and the respective window 30 or 34.

The design of the cell assembly makes assembly of the unit relatively easy. All components are self-locating such that the parts are stacked together in the proper order.

The present invention provides an improved form of cell assembly, and particularly one which serves as a reliable and repeatable device for performing absorbance detection at a sensitive level in supercritical fluid chromatography, as well as other applications. Appropriate sealing is provided by applying two forces to different parts of a sealing member (washer) to suitably seal the sealing member with a cell body and the window therefor.

While embodiments of the present invention have been shown and described, various modifications may be made without departing from the scope of the present invention, and all such modifications and equivalents are intended to be covered.

What is claimed is:

1. A cell assembly including a cell body and a cell window for containing a sample volume to be analyzed, the improvement comprising means for providing a seal across the interface of the cell window and cell body comprising
    sealing means disposed adjacent and overlying the interface of the cell window and cell body, and
    loading means for applying a load to said sealing means with a first force being applied between the sealing means and the cell window and a second force being applied between the sealing means and the cell body, said loading means comprising two independent loading elements for providing said two forces.

2. A cell assembly as in claim 1, wherein said sealing means comprises a metallic sealing member.

3. A cell assembly as in claim 2 wherein said sealing member is formed of a soft metal and plated with an inert metal.

4. A cell assembly including a cell body for containing a sample volume of a substance through which electromagnetic radiation can be transmitted for the purpose of spectrophotometric analysis or detection of a substance within the sample volume, comprising
    the cell body including a sample bore forming a volume and pathlength for fluid to flow through, and including passageways for fluid flow into and out of the sample bore, the cell body having a first recess, and having a second, larger recess forming a shoulder,
    an electromagnetic transmissive window disposed in said first recess for allowing electromagnetic radiation to pass through the sample bore and the window,
    sealing means disposed in said second recess and abutting said shoulder in the cell body and abutting a surface of the window remote from the sample bore, and
    loading means engaging the sealing means at inner and outer locations thereof along the sealing means for causing the sealing means to (i) seal against an outer surface of the window, and (ii) seal against the shoulder of said body to thereby form seals between the sealing means and the window and the body.

5. An assembly as in claim 4 wherein
    said sealing means comprises a circular seal washer formed of a soft metal and plated with an inert metal.

6. An assembly as in claim 5 wherein
    said seal washer is formed of soft copper and plated with gold, and said seal washer includes an aperture therethrough for transmission of said radiation, and includes a rim for engaging and abutting against said window.

7. An assembly as in claim 4 wherein said loading means comprises
    ring means for engaging an outer portion of said sealing means,
    spring loaded means for engaging an inner portion of said sealing means, and
    cap means for pressing said ring means and said spring means toward said cell body.

8. An assembly as in claim 7 wherein said spring loaded means comprises
    plunger means engaging the inner portion of said sealing means, and Belleville washer means engaging and bearing against said plunger means.

9. A cell assembly including a cell body for containing a sample volume of a substance through which electromagnetic radiation can be transmitted for analysis, comprising
    the cell body including a sample bore forming a volume and pathlength for fluids to flow through, and including passageways for fluid flow into and out of the sample bore, the cell body having a first recess and having a second larger recess forming a shoulder, an electromagnetic transmissive window disposed in said first recess for allowing electromagnetic radiation to pass through the sample bore and the window, a sealing washer disposed in said second recess and having an outer radial portion engaging said shoulder in the cell body, and having an inner radial portion including a circular projection for engaging a radially inner surface of the window remote from the sample bore, said sealing washer having an aperture therein through which said radiation can pass, and said sealing washer being formed of soft material and having at least a surface inert to a sample to be passed through said sample bore, first loading means engaging the sealing washer at a radially outer portion thereof for causing the sealing washer to engage said shoulder in the cell body to provide a seal between the sealing washer and the cell body, second loading means engaging a radially inner portion of the sealing washer for causing said circular projection of the sealing washer to engage a surface of the window remote from the sample bore to thereby provide a seal between the sealing washer and the window, said second loading means comprising plunger means for engaging the sealing washer and spring means for pressing the plunger means toward said sealing washer, and cap means for engaging both said first and second loading means to load the same toward the cell body.

10. An assembly as in claim 9 wherein
said sealing means comprises a circular sealing washer formed of a soft metal and plated with an inert metal.

11. A cell assembly including a cell body and a cell window for containing a sample volume to be analyzed, the improvement comprising means for providing a seal across the interface of the cell window and cell body comprising sealing means disposed adjacent the interface of the cell window and cell body, loading means for applying a load to said sealing means with a first force being applied between the sealing means and the cell window and a second force being applied between the sealing means and the cell body, said loading mean comprising two independent loading elements for providing said two forces, wherein said first independent loading element comprises spring loaded means for engaging an inner portion of said sealing means for applying said first force, and said second independent loading element comprises ring means for engaging an outer portion of said sealing means for applying said second force, and said loading means includes cap means for pressing said spring means and said ring means toward said cell body.

12. A cell assembly including a cell body and a cell window for containing a sample volume to be analyzed, the improvement comprising means for providing a seal across the interface of the cell window and cell body comprising sealing means disposed adjacent the interface of the cell window and cell body, said sealing means overlying said interface and having a first side engaging both said cell window and cell body, and loading means for applying loads to a second side of said sealing means with a first force being applied between the sealing means and the cell window and a second force being applied between the sealing means and the cell body, said loading means comprising two independent loading elements for providing said two forces.

* * * * *

UNITED STATES PATENT AND TRADEMARK OFFICE
CERTIFICATE OF CORRECTION

PATENT NO. : 5,054,919

DATED : October 8, 1991

INVENTOR(S) : Raymond G. Bryan

It is certified that error appears in the above-identified patent and that said Letters Patent is hereby corrected as shown below:

Column 8, line 37, "seal" washer should be --sealing washer--.

Signed and Sealed this

Eighth Day of November, 1994

Attest:

BRUCE LEHMAN

Attesting Officer

Commissioner of Patents and Trademarks